United States Patent
Runge et al.

(10) Patent No.: US 6,287,615 B1
(45) Date of Patent: Sep. 11, 2001

(54) USE OF SOLUBILIZED CAROTENOID PREPARATIONS FOR COLORING FOOD PREPARATIONS

(75) Inventors: Frank Runge, Maxdorf; Georg Konrad Zwissler, Bad Dürkheim; Lutz End, Mannheim; Loni Schweikert, Altrip; Dieter Horn, Heidelberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/989,135

(22) Filed: Dec. 11, 1997

(30) Foreign Application Priority Data

Dec. 20, 1996 (DE) .............................. 196 53 410

(51) Int. Cl.$^7$ .................................. A23L 1/272
(52) U.S. Cl. ........................ 426/268; 426/580; 426/607
(58) Field of Search ............................ 424/600; 514/937, 514/943, 763; 426/72, 74, 262, 540, 541, 590, 580, 603, 250, 607, 268

(56) References Cited

U.S. PATENT DOCUMENTS

| | | | |
|---|---|---|---|
| 3,110,598 | 11/1963 | Muller | 99/148 |
| 3,886,294 | 5/1975 | Emodi et al. | 426/540 |
| 4,366,151 | 12/1982 | Oppenlaender | 514/763 |
| 4,435,427 | 3/1984 | Hoppe et al. | 424/356 |
| 4,522,743 | 6/1985 | Horn et al. | 252/311 |
| 5,350,773 | 9/1994 | Schweikert et al. | 424/238 |
| 5,364,563 | 11/1994 | Cathrein et al. | 252/311 |
| 5,453,447 | 9/1995 | End et al. | 514/763 |
| 5,886,053 | * 3/1999 | Schmutzler et al. | 514/763 |
| 5,891,907 | * 4/1999 | Kolter et al. | 514/458 |
| 5,925,684 | * 7/1999 | Schweikert et al. | 514/941 |

FOREIGN PATENT DOCUMENTS

| | | |
|---|---|---|
| 2199415 | 9/1997 | (CA) . |
| 2411529 | 3/1974 | (DE) . |
| 800825 | 10/1997 | (EP) . |
| 10120933 | 5/1998 | (JP) . |
| 91/06292 | 5/1991 | (WO) . |
| 94/06310 | 3/1994 | (WO) . |
| 94/19411 | 9/1994 | (WO) . |

OTHER PUBLICATIONS

Fiedler, Lexicon der Hilfsstoffe fur Pharmazie, *Kosmetic und ang. Gebiete*, pp. 537–545 and 753–756.

* cited by examiner

*Primary Examiner*—Keith Hendricks
(74) *Attorney, Agent, or Firm*—Keil & Weinkauf

(57) ABSTRACT

The use of solubilized carotenoid preparations is described for coloring foods, wherein solubilized carotenoid preparations are used which are produced by heating a suspension comprising from 1 to 40% by weight of one or more carotenoids, from 20 to 90% by weight of one or more nonionogenic emulsifiers and from 0 to 50% by weight of other additives to from 120 to 200° C. for a short time and turbulently mixing the homogeneous solution with amounts of water or an aqueous solution comprising hydrophilic antioxidants with or without other surface-active additives at from 10 to 95° C. to form a solubilized preparation having a carotenoid content of from 0.5 to 10% by weight.

15 Claims, No Drawings

USE OF SOLUBILIZED CAROTENOID PREPARATIONS FOR COLORING FOOD PREPARATIONS

The present invention relates to the use of solubilized carotenoid preparations having a carotenoid content of from 0.5 to 10% by weight for coloring foods and pharmaceutical preparations.

Carotenoids are a group of color pigments of yellow to red hue, which occur widely in nature and give many foods a characteristic color. The most important representatives of this class of substances are β-carotene, β-apo-8'-carotenal, canthaxanthin, astaxanthin, lycopene and citranaxanthin. These substances which may be prepared synthetically are important colorants both for the food industry and pharmaceutical technology as substitutes for synthetic dyes, for example, and are of interest, in part, because of their provitamin A activity.

All carotenoids are insoluble in water, whereas in fats and oils a still only low solubility is found. This limited solubility and the high sensitivity to oxidation impede direct application of the relatively coarse-grained products obtained from synthesis in coloring foods, since the substances in coarsely crystalline form give only poor coloring results.

To improve the color yields, various processes have been described, all of which have the purpose of reducing the crystallite size of the active compounds and bringing it to a particle size range of below 10 μm. In addition to grinding carotenoids, in accordance with WO 91/06292 and WO 94/19411, these processes include, for example, the known emulsifying and micronizing processes, described inter alia in DE-A-12 11 911, EP-A-0 410 236 and in EP-B-0 065 193.

For specific fields of application of carotenoids, for example for coloring beverages (including soft drinks) it is desired that the carotenoid formulation is present in liquid form and that the redispersion of this liquid formulation in aqueous systems leads to solutions with clear colors. To achieve this effect, correspondingly small active compound particles (<100 nm) are required.

EP-A-0 551 638 describes emulsions of β-carotene which are stabilized with ascorbyl palmitate as emulsifier, whose particle size is still between 200 and 300 nm.

Furthermore, WO 94/06310 describes solubilized carotenoid preparations for beverage coloration whose active compound content is at most 1.0% by weight, however.

It is an object of the present invention, therefore, to propose stable solubilized carotenoid preparations for coloring foods and pharmaceutical preparations, whose particle size is in the range from 10 to 200 nm and whose active compound concentration is greater than 0.5% by weight.

We have found that this object is achieved according to the invention by using solubilized carotenoid preparations for coloring foods and pharmaceutical preparations, wherein solubilized carotenoid preparations are used which are produced by heating a suspension comprising from 1 to 40% by weight of one or more carotenoids, from 20 to 90% by weight of one or more nonionogenic emulsifiers and from 0 to 50% by weight of other additives to from 120 to 200° C. for a short time and turbulently mixing the homogeneous solution with amounts of water or an aqueous solution comprising hydrophilic antioxidants with or without other surface-active additives at from 10 to 95° C. to form a solubilized preparation having a carotenoid content of from 0.5 to 10% by weight. The solubilized preparation may be diluted further to a desired final concentration.

The use according to the invention of the solubilized carotenoid-containing preparations in food coloring enables a broad color spectrum to be covered, since, on the basis of concentrated active compound formulations, the desired coloring effect can be adjusted via the amount of the corresponding carotenoid-containing formulation.

The solubilized preparations employed for the use according to the invention as food colorant can be prepared either batchwise, according to EP-A-0 055 817, or else, in particular, continuously, according to the process described in EP-A-0 479 066. A suspension, preferably preheated to from 20 to 80° C., preferably from 50 to 70° C., of from 1 to 40% by weight, preferably from 10 to 30% by weight, of one or more carotenoids in 20 to 90% by weight of one or more nonionogenic emulsifiers, with or without the addition of from 0 to 50% by weight of other additives, is pumped through a heating coil situated in a thermal oil, the temperature in the solubilizing mixture being from 120 to 2000° C. and the residence time from 10 to 300 seconds, and the homogeneous solution being turbulently mixed in a mixing chamber, if appropriate under a pressure elevated to from 10 to 50 bar, with amounts of water or an aqueous solution comprising hydrophilic antioxidants with or without other surface-active additives, from 10 to 95° C., to give a rapid cooling of the homogeneous solution to below 95° C. and to form a solubilized preparation having a carotenoid content of from 0.5 to 10% by weight, preferably from 1.5 to 6% by weight.

With regard to more precise process descriptions, the two abovementioned European patents and the conditions described there are expressly incorporated herein by reference.

The carotenoids which can be employed in the procedure of the invention are the known, obtainable, natural or synthetic representatives of this class of compounds which are usable as coloring means, e.g. β-carotene, lycopine, bixin, zeaxanthin, cryptoxanthin, citranaxanthin, lutein, canthaxanthin, astaxanthin, β-apo-4'-carotenal, β-apo-8'-carotenal, β-apo-12'-carotenal, β-apo-8'-carotenic acid and esters of hydroxy- and carboxy-containing representatives of this group, e.g. the lower alkyl esters and preferably the methyl esters and ethyl esters. Particularly preferably, the previously readily industrially obtainable representatives are used, such as β-carotene, canthaxanthin, astaxanthin, lycopine, β-apo-8'-carotenal and β-apo-8'-carotenic esters.

The carotenoids can be suspended in emulsifier either in pure form or else in the form of an oily dispersion, where the dispersant can be of mineral, vegetable or animal origin. Typical representatives are edible oils, in particular sesame seed oil, corn oil, cotton seed oil, soya bean oil or peanut oil.

Suitable emulsifiers are nonionogenic emulsifiers, which are known per se, having an HLB value (cf. H. P. Fiedler, Lexikon der Pharmazie, Kosmetik und angrenzende Gebiete, [Lexicon of Pharmacy, Cosmetics and related areas], 1996, pages 753–756) of from 12 to 16, in particular ethoxylated triglycerides of fatty acids having from 12 to 18 carbons which contain from 20 to 60 ethoxy units or ethoxylated sorbitan fatty acid esters having approximately 20 ethoxy units or ethoxylated monohydroxy fatty acids having from 14 to 17 ethoxy units, as are described in DE-A-29 11 241. Emulsifiers of this type are also called solubilizers, because they dissolve in water and thus act as solubilizers for lipophilic substances, by keeping these in micellar solution. Micellar solutions are characterized by transparency and clarity. They can be characterized by reporting the particle size of the micelles, determined by quasi-elastic light scattering.

Corresponding diameters are from 10 to 200 nm, depending on the solubilizer used and active compound content.

Particularly suitable examples of nonionogenic emulsifiers are: glycerol polyoxyethylene glycol ricinoleate, glycerol polyoxyethylene glycol oxystearate, polyoxyethylene (20) sorbitan monooleate, polyoxyethylene(20) sorbitan monostearate, polyoxyethylene(20) sorbitan monopalmitate and monohydroxystearic acid containing 15 ethoxy units, which are used in a concentration of from 100 to 1000% by weight, preferably from 300 to 800% by weight, based on the carotenoid employed.

To improve the antifoam properties of the solubilized preparations, in addition to the solubilizers described above, other surface-active substances can be employed, preferably in a concentration of from 0 to 5% by weight, based on the total amount of the solubilized preparation. In addition to fatty alcohols, oils, polymers such as polysiloxanes and phospholipids such as lecithin, these are preferably emulsifiers having an HLB value of less than 5 which act as defoamers. These antifoamers can be added during production of the solubilized preparation, depending on solubility, either to the solubilizer/carotenoid mixture or to the aqueous phase. However, it is also possible to add the defoamer separately and not until after production of the solubilized preparation.

To protect the carotenoids against oxidative decomposition and thus to increase the light stability of the solubilized preparations used, antioxidants can additionally be conjointly used. Examples of customary antioxidants which may be used in the solubilized preparation individually or as a mixture in amounts of from 0 to 500% by weight, in the case of water-soluble antioxidants, and from 0 to 200% by weight, in the case of oil-soluble antioxidants, based on the carotenoid employed, are: butylated hydroxytoluene, butylated hydroxyanisole, ascorbyl palmitate, ascorbic acid, sodium ascorbate and d, 1-α-tocopherol and d,1-α-tocopherol esters.

In the case of tocopherol-containing solubilized preparations, surprisingly, large amounts of ascorbic acid and sodium ascorbate could be dissolved in the aqueous phase without precipitates occurring in the solubilized preparation. Apart from an additional vitamin C enrichment of this liquid carotenoid formulation, this has the advantage that these water-soluble antioxidant components, on diluting the solubilized preparations with oxygen-containing water or an aqueous system to the user concentration of approximately from 1 to 100 ppm of carotenoid, can efficiently trap the dissolved oxygen, so that the carotenoids remain protected.

The solubilized preparations according to the invention comply with the requirements of microbiological testing for microbial count determination according to DAB 10 (DAB: Deutsches Arzneibuch, [German Pharmacopoeia). According to this, the reduction of all test microorganisms exceeds the DAB requirements for the preservation properties of oral preparations. Furthermore, by adding preservatives approved for food use, such as sorbic acid, sodium sorbate, benzoic acid, sodium benzoate, benzyl alcohol, butylated hydroxytoluene or PHB esters such as 4-hydroxymethylbenzoate or 4-hydroxypropylbenzoate in a concentration of from 0 to 200% by weight, preferably from 10 to 150% by weight, particularly preferably from 15 to 80% by weight, based on the carotenoid(s), undesired microbial decomposition of the solubilized preparation, which cannot always be excluded during a prolonged storage time, can be prevented.

A further possibility for avoiding microbiological growth during long storage times is reducing the water activity in the solubilized preparation by adding sugars and/or sugar alcohols, such as sucrose, glucose, fructose, lactose, invert sugar, sorbitol, mannitol or glycerol.

Continuous production of solubilized preparations leads to aqueous dispersions of very small micelles having a mean particle diameter of from 10 to 200 nm, preferably less than 100 nm, the carotenoid(s) being present in dissolved form in the micelle interior. Surprisingly, despite the high active compound concentration of up to 10% by weight, the solubilized preparations are physically and chemically stable. Precipitation of the carotenoids which are water-insoluble per se, was not observed even at the high concentrations both of active compounds and of additives.

The use of the concentrated solubilized carotenoid preparations is predominantly in the sector of food coloring, specifically in pigmenting beverages which must remain optically clear. The solubilized preparations are very highly compatible both with ascorbic acid, as mentioned above, and with other acids customary in the food and beverage industry, such as fruit acids. In addition, fats, such as butter and margarine, and milk products can be colored with these liquid carotenoid formulations.

The examples illustrate the invention.

EXAMPLE 1

A suspension, preheated to 65° C., of 500 g of β-carotene in 2500 g of polyoxyethylene(20) sorbitan monostearate (Tween® 60) was fed at a throughput of 2.2 kg/h into a heating coil which was immersed in an oil bath heated to 190° C. and had an internal diameter of 2 mm and a length of 12 m. At 164° C. on exit from the heat exchanger and after a residence time of 62 s, the β-carotene was dissolved in the emulsifier. In a connected mixing chamber, the β-carotene solution was turbulently mixed with water at 25° C. (throughput: 5.4 kg/h) at a mixing temperature of 62° C. The solubilized preparation was discharged at 20 bar via a pressure control valve. A dark red micellar β-carotene solution having a β-carotene content of 4.4% by weight and a micelle size of 20 nm was obtained.

EXAMPLE 2

A suspension, preheated to 70° C., of 500 g of β-carotene in 2300 g of polyoxyethylene(20) sorbitan monostearate (Tween® 60) and 207 g of d,1-α-tocopherol was fed, at a throughput of 2.2 kg/h, into a heating coil which was immersed in an oil bath heated to 190° C. and had an internal diameter of 2 mm and a length of 12 m. At 164° C., on exit from the heat exchanger and after a residence time of 62 s, the β-carotene was dissolved in the emulsifier. In a connected mixing chamber, the β-carotene solution was turbulently mixed with water at 25° C. (throughput: 5.4 kg/h) at a mixing temperature of 61° C. The solubilized preparation was discharged at 20 bar via a pressure control valve. A dark red micellar β-carotene solution having a β-carotene content of 4.4% by weight and a tocopherol content of 2.0% by weight was obtained. The mean micelle size was 29 nm.

EXAMPLE 3

Solubilization was performed in a similar manner to Example 1. The aqueous phase used in each case was a 10, 20 or 30% strength by weight aqueous glycerol solution. The experimental results are summarized in Table 1.

TABLE 1

|  | 10% by wt. glycerol | 20% by wt. glycerol | 30% by wt. glycerol |
|---|---|---|---|
| Throughput of suspension [kg/h] | 2.2 | 2.2 | 2.3 |
| Throughput of aqueous phase [kg/h] | 5.4 | 5.4 | 5.4 |
| β-carotene content [% by weight] | 4.4 | 4.4 | 4.6 |
| Micelle size [nm] | 17 | 18 | 28 |

EXAMPLE 4

The experimental procedure was performed in a similar manner to Example 2. The influence of different amounts of d,1-α-tocopherol on the properties of the solubilized preparation was studied in three different experiments. The experimental results are summarized in Table 2.

TABLE 2

|  | 0.5% by wt. tocopherol | 3.0% by wt. tocopherol | 4.0% by wt. tocopherol |
|---|---|---|---|
| Throughput of suspension [kg/h] | 2.2 | 2.2 | 2.3 |
| Throughput of aqueous phase [kg/h] | 5.4 | 5.4 | 5.4 |
| β-carotene content [% by weight] | 4.5 | 3.6 | 3.9 |
| Micelle size [nm] | 17 | 74 | 95 |

EXAMPLE 5

The experimental procedure was performed in a similar manner to Example 2. Instead of water, a solution of 200 g of ascorbic acid and 200 g of sodium ascorbate per kg of water was used. The resulting solubilized preparation had the following composition: 3.9% by weight of β-carotene, 2.0% by weight of tocopherol, 9.9% by weight of sodium ascorbate, 9.9% by weight of ascorbic acid. Micelle size: 19 nm.

EXAMPLE 6

A suspension, preheated to 500° C., of 200 g of a 20% strength by weight dispersion of apocarotenal in peanut oil in 480 g of polyoxyethylene(20) sorbitan monostearate (Tween® 60) and 16 g of tocopherol were fed, at a throughput of 1.0 kg/h, to a heating coil which was immersed in an oil bath heated to 170° C. and had an internal diameter of 2 mm and a length of 12 m. At 138° C. on exit from the heat exchanger and after a residence time of 136 s, the apocarotenal was dissolved in the emulsifier. In a connected mixing chamber, the apocarotenal solution was turbulently mixed with water at 25° C. (throughput: 8.3 kg/h) at a mixing temperature of 40° C. The solubilized preparation was discharged at 30 bar via a pressure control valve. A dark red micellar apocarotenal solution having an apocarotenal content of 0.59% by weight, a d,1-α-tocopherol content of 0.25% by weight and a micelle size of 21 nm was obtained.

EXAMPLE 7

A suspension, preheated to 50° C., of 40 g of apocarotenal in 500 g of polyoxyethylene(20) sorbitan monopalmitate (Tween®40) and 32 g of d,1-α-tocopherol was fed, at a throughput of 1.0 kg/h, into a heating coil which was immersed in an oil bath heated to 180° C. and had an internal diameter of 2 mm and a length of 12 m. At 150° C. on exit from the heat exchanger and after a residence time of 136 s, the apocarotenal was dissolved in the emulsifier. In a connected mixing chamber, the apocarotenal solution was turbulently mixed with water at 25° C. (throughput: 8.3 kg/h) at a mixing temperature of 40° C. The solubilized preparation was discharged at 30 bar via a pressure control valve. A dark red micellar apocarotenal solution having an apocarotenal content of 0.6% by weight, a d,1-α-tocopherol content of 0.6% by weight and a micelle size of 35 nm was obtained.

EXAMPLE 8

One part by volume of solubilized preparation from Example 1 was mixed with the same volume of a 1% strength by weight aqueous solution of a defoamer, shaken under defined conditions for 30 s, and the height of the foam crown was measured in cm as a function of time under a defined geometry. As a comparison, the solubilized preparation was mixed with the same volume of water. Table 3 shows that when the defoamer was added, significantly less foam formation and/or more rapid breakdown of the foam formed was observed.

TABLE 3

| Defoamer | Foam height (start) [cm] | Foam height (5 min) [cm] | Foam height (10 min) [cm] |
|---|---|---|---|
| None | 2.5 | 1.5 | 1.0 |
| Sorbitan monopalmitate | 1.5 | 1.4 | 1.3 |
| Acetic ester of mono-/diglycerides | 3.0 | 1.0 | 0.7 |
| Lecithin | 1.0 | 0.8 | 0.7 |

EXAMPLE 9

100 g of fructose, 5 g of citric acid and 1 g of vitamin C were dissolved in 800 g of water in a glass beaker. In a second glass beaker, 15 ml of orange essence and 65 mg of a 4% strength by weight β-carotene solubilized preparation were emulsified into a solution of 0.25 g of xanthan in 100 g of water, and the mixture was homogenized using an Ultraturrax "T25" for 2 minutes at 1000 rpm. The contents of both glass beakers were then combined with stirring, the mixture was pasteurized via a short-time heater unit and charged into bottles. The beverage had a clear brilliant yellow color and a β-carotene content of 2.5 ppm.

We claim:

1. A method of coloring a food preparation with a carotenoid by admixing an effective amount of a carotenoid preparation with the food preparation, wherein the carotenoid preparation is an aqueous composition comprising of from 3.6 to 10% by weight of one or more carotenoids in the form of micelles, said aqueous composition being obtained by
   i) heating a suspension comprising
      a) from 1 to 40% by weight of one or more carotenoids,
      b) from 20 to 90% by weight of one or more non-ionic emulsifiers, and
      for from 10 to 300 seconds to from 120 to 180° C. to give a homogenous carotenoid solution, and subsequently
   ii) turbulently mixing the homogenous carotenoid solution at from 10 to 95° C. with an aqueous solution of a hydrophilic antioxidant selected from the group consisting of ascorbic acid, sodium ascorbate and mixtures thereof, wherein the hydrophilic antioxidant is present in an amount of at least 10% by weight, based on the total weight of carotenoids.

2. The method of claim 1, wherein the aqueous solution which is admixed with the homogenous carotenoid solution further comprises one or more conventional surface-active additives.

3. The method of claim 1, wherein the carotenoid preparation comprises up to 6% by weight of one or more carotenoids.

4. The method of claim 1, wherein the non-ionic emulsifiers have an HLB value of from 12 to 16.

5. The method of claim 1, wherein the non-ionic emulsifiers are present in an amount of from 100 to 1000% by weight, based on the total weight of carotenoids.

6. The method of claim 5, wherein the non-ionic emulsifiers are present in an amount of from 300 to 800% by weight.

7. The method of claim 4, wherein a combination of non-ionic emulsifiers is used as component b), said combination comprising non-ionic emulsifiers having an HLB value of less than 5.

8. The method of claim 1, wherein the hydrophilic antioxidant is present in an amount of up to 500% by weight, based on the total weight of carotenoids.

9. The method of claim 1, wherein the hydrophilic antioxidant is present in an amount of up to 200% by weight, based on the total weight of carotenoids.

10. The method of claim 1, wherein the micelles have a particle size of from 10 to 200 nm.

11. The method of claim 10, wherein the micelles have a particle size of less than 100 nm.

12. The method of claim 1, wherein the food preparation is a beverage.

13. The method of claim 1, wherein the food preparation is a margarine or a milk product.

14. The method of claim 1, wherein the hydrophilic antioxidant is present in an amount of at least 15% by weight, based on the total weight of carotenoids.

15. The method of claim 1, wherein the food preparation is selected from the group of beverages, fats and milk products.

* * * * *